US010631948B2

(12) United States Patent
Miyamoto (10) Patent No.: US 10,631,948 B2
(45) Date of Patent: Apr. 28, 2020

(54) IMAGE ALIGNMENT DEVICE, METHOD, AND PROGRAM

(71) Applicant: FUJIFILM Corporation, Tokyo (JP)

(72) Inventor: Masaki Miyamoto, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 30 days.

(21) Appl. No.: 15/259,753

(22) Filed: Sep. 8, 2016

(65) Prior Publication Data

US 2017/0091554 A1    Mar. 30, 2017

(30) Foreign Application Priority Data

Sep. 29, 2015  (JP) ................................ 2015-190659

(51) Int. Cl.
*A61B 90/00* (2016.01)
*G06T 11/60* (2006.01)
*G06T 7/33* (2017.01)
*G06K 9/62* (2006.01)
*A61B 34/20* (2016.01)

(52) U.S. Cl.
CPC ............ *A61B 90/361* (2016.02); *G06T 7/337* (2017.01); *G06T 11/60* (2013.01); *A61B 2034/2048* (2016.02); *A61B 2090/365* (2016.02); *A61B 2090/373* (2016.02); *G06K 9/6207* (2013.01); *G06T 2200/04* (2013.01); *G06T 2207/20092* (2013.01); *G06T 2207/30056* (2013.01)

(58) Field of Classification Search
CPC .. A61B 34/20; A61B 2090/364; A61B 8/5238
See application file for complete search history.

(56) References Cited

U.S. PATENT DOCUMENTS

| 8,059,878 B2 * | 11/2011 | Feilkas | A61B 90/36 382/131 |
| 8,641,621 B2 * | 2/2014 | Razzaque | A61B 34/20 600/407 |
| 8,672,836 B2 * | 3/2014 | Higgins | A61B 1/00009 345/427 |

(Continued)

FOREIGN PATENT DOCUMENTS

| JP | 2007-268259 A | 10/2007 |
| JP | 2008-68086 A | 3/2008 |

(Continued)

*Primary Examiner* — Nay A Maung
*Assistant Examiner* — Jose Torres
(74) *Attorney, Agent, or Firm* — Birch, Stewart, Kolasch & Birch, LLP (57) ABSTRACT

There is provided an image registration device, method, and program that enable easy initial registration between a target object included in a video and a simulation image. A first registration unit performs first registration that is initial registration between an intraoperative video and a simulation image. At this time, a boundary image showing the boundary of the simulation image is displayed on a display so as to be superimposed on the intraoperative video. An operator performs registration between a target object included in the intraoperative video and the boundary image. After the end of the first registration, a second registration unit performs second registration between the simulation image and the target object included in the intraoperative video based on the result of the first registration.

10 Claims, 5 Drawing Sheets

(56) References Cited

U.S. PATENT DOCUMENTS

| | | | |
|---|---|---|---|
| 8,798,346 B2* | 8/2014 | Cizek | G06T 7/33 378/62 |
| 9,547,940 B1* | 1/2017 | Sun | G06T 19/006 |
| 2004/0153128 A1* | 8/2004 | Suresh | G06F 19/3481 607/14 |
| 2007/0018975 A1* | 1/2007 | Chuanggui | A61B 90/36 345/419 |
| 2007/0223794 A1 | 9/2007 | Preiss et al. | |
| 2008/0069436 A1 | 3/2008 | Orderud | |
| 2008/0118132 A1* | 5/2008 | Ubelhart | A61B 6/032 382/131 |
| 2009/0012390 A1* | 1/2009 | Pescatore | A61B 6/12 600/425 |
| 2009/0048611 A1* | 2/2009 | Funda | A61B 1/00193 606/130 |
| 2010/0156904 A1* | 6/2010 | Hartung | G06T 17/00 345/420 |
| 2012/0253170 A1 | 10/2012 | Kim et al. | |
| 2013/0172731 A1* | 7/2013 | Gole | A61B 5/0035 600/424 |
| 2013/0218002 A1* | 8/2013 | Kiraly | G01R 33/4814 600/411 |
| 2014/0241600 A1* | 8/2014 | Mountney | G06T 17/00 382/128 |
| 2015/0051617 A1 | 2/2015 | Takemura et al. | |
| 2015/0287236 A1* | 10/2015 | Winne | G06F 3/147 382/128 |
| 2015/0342739 A1 | 12/2015 | Mahfouz | |
| 2015/0374260 A1* | 12/2015 | Govari | G01R 33/285 600/417 |
| 2016/0081658 A1* | 3/2016 | Perrey | A61B 8/5238 600/440 |
| 2017/0084036 A1* | 3/2017 | Pheiffer | G06T 7/337 |

FOREIGN PATENT DOCUMENTS

| | | |
|---|---|---|
| JP | 2010-200894 A | 9/2010 |
| JP | 2010-259497 A | 11/2010 |
| JP | 2012-518520 A | 8/2012 |
| JP | 2012-205899 A | 10/2012 |
| JP | 2013-202313 A | 10/2013 |

* cited by examiner

IMAGE ALIGNMENT DEVICE, METHOD, AND PROGRAM

CROSS-REFERENCE TO RELATED APPLICATIONS

The present application claims priority under 35 U.S.C. § 119 to Japanese Patent Application No. 2015-190659, filed on Sep. 29, 2015, all of which are hereby expressly incorporated by reference into the present application.

BACKGROUND OF THE INVENTION

1. Field of the Invention

The present invention relates to an image registration device, method, and non-transitory computer readable medium storing a program for performing registration between a target object included in a video and a simulation image relevant to the target object.

2. Description of the Related Art

In recent years, surgical simulation using a three-dimensional medical image has been actively performed. Surgical simulation is for visualizing surgery target tissue, organs, and surrounding structures thereof in a medical image and simulating the procedure performed in actual surgery. For example, in a partial resection simulation of the liver, a simulation image viewed from the operative field at the time of surgery is generated by extracting tissues, such as the liver, the portal vein, veins, arteries, the body surface, bone, and a tumor, from a computed tomography (CT) image or a magnetic resonance imaging (MRI) image and visualizing the tissues as a three-dimensional image. Then, a range for excising a tumor in the liver is calculated by a computer using the simulation image, and a surgical plan is made to perform the surgery.

On the other hand, there is a desire to see the simulation image during surgery. For this reason, paper on which a simulation image is printed is brought to the operating room, or the simulation image is displayed on a display installed in the operating room. Then, a doctor performs the surgery while watching the operative part of the actual patient and while viewing the simulation image printed on paper or displayed on the display for the sake of confirmation.

However, it is very troublesome to perform the surgery while alternately viewing the patient and the simulation image. Therefore, a method of acquiring a video including a plurality of images by imaging a surgery target part during surgery and displaying a simulation image so as to be superimposed on the video has been proposed. For example, JP2013-202313A has proposed a method of attaching an optical sensor or a magnetic sensor directly to a camera for imaging an operative part, a surgical instrument, or an organ, performing a calibration, that is, initial registration of the relative positional relationship therebetween, registrating a surgery target part and a simulation image by moving the simulation image with respect to changes in the position and orientation of the camera and the movement of the organ after the initial registration, and displaying the surgery target part and the simulation image after the registration so as to be superimposed on each other.

In addition, a method of placing a marker in a surgery target part, detecting the position of the marker using a sensor, registrating the surgery target part and a simulation image, and displaying the surgery target part and the simulation image after the registration on a head mounted display (refer to JP2010-259497A) and a method of embedding a marker in a surgery target part, detecting the marker using a sensor, registrating the surgery target part and a simulation image, and displaying the surgery target part and the simulation image after the registration on a monitor (refer to JP2010-200894A) have also been proposed.

On the other hand, a method of registrating an image of a patient who has been captured and a simulation image without using a sensor or the like has also been proposed. For example, JP2012-205899A has proposed a method in which, when generating an organ model from a three-dimensional image and displaying the organ model so as to be superimposed on an ultrasound image in real time, an affine transformation function between each frame of the ultrasound image and the organ model is calculated, the organ model is converted based on the affine transformation function, and the converted organ model is superimposed on the ultrasound image. JP2012-518520A has proposed a method of performing registration between an image of the bone and a template configured to include the contour of the bone. JP2007-268259A has proposed a method of performing registration between the wire-frame model of a three-dimensional image and a target object. JP2008-068086A has proposed a method of performing registration between an ultrasound image and a contour model by superimposing the contour model on the ultrasound image.

SUMMARY OF THE INVENTION

By the methods disclosed in JP2012-518520A, JP2007-268259A, and JP2008-068086A, it is possible to easily perform registration between a target object and a simulation image, such as a template or a wire-frame model. However, the methods disclosed in JP2012-518520A, JP2007-268259A, and JP2008-068086A are relevant to registration after initial registration between the target object and the simulation image. Here, when imaging a target object, as long as the camera is held by the hand, it is difficult to hold the camera completely still. Accordingly, the target object moves in a displayed video. For this reason, it is very difficult for the operator to manually perform initial registration between the target object included in the video and the simulation image. In particular, if the simulation image overlaps the target object, initial registration becomes very difficult since it is difficult to see the target object.

The invention has been made in view of the aforementioned situation, and it is an object of the invention to enable easy initial registration between a target object included in a video and a simulation image.

A first image registration device according to the invention comprises: image acquisition unit that acquires a video configured to include two or more images with different imaging times that include a target object to be imaged; simulation image acquisition unit that acquires a simulation image relevant to the target object; boundary image acquisition unit that acquires a boundary image showing a boundary of the simulation image; display control unit that displaying the video and the simulation image on display unit; and first registration unit that performs first registration between the target object included in the video and the simulation image in response to an instruction for the first registration. The display control unit displays the boundary image on the display unit instead of the simulation image while an instruction of at least the first registration is given.

"Simulation image" means an arbitrary image that is relevant to the target object and includes information indicating the outer shape of the target object. For example, in a case where the target object is a surgery target part, an image showing the three-dimensional shape of the target part and an image showing the three-dimensional shapes of the target part and a structure included in the target part can be used as simulation images. In addition, images, such as a functional three-dimensional image acquired by positron emission tomography (PET) examination or nuclear medical (NM) examination, can be used as simulation images as long as the information indicating the outer shape of the target object is included.

"Instruction of the first registration" means an instruction to match the simulation image with the target object included in the video by changing the simulation image by at least one of parallel movement, rotational movement, and enlargement and reduction, and its orientation. "Changing the orientation" means rotating the simulation image around the axis parallel to the display surface of the display means or the axis along the display surface. On the other hand, "rotational movement" means rotation around the axis perpendicular to the display surface of the display unit.

"First registration" is not limited to the initial registration described above, and a case of performing registration again in response to an instruction of the first registration while second registration to be described later is being performed after the end of the first registration is also included in the first registration.

"Boundary of the simulation image" means, in the simulation image displayed on the display unit, a boundary between the simulation image and a portion other than the simulation image. In a case where the simulation image is a three-dimensional image, the form of the simulation image may be changed if the orientation of the simulation image is changed. In such a case, a boundary image is generated by extracting the boundary according to the orientation change.

"Displaying a boundary image instead of a simulation image while an instruction of at least the first registration is given" includes displaying a boundary image while an instruction of the first registration is given, that is, only while the operator is performing an operation of the first registration and displaying a boundary image continuously until the first registration ends even in a state in which the instruction of the first registration has been stopped.

The first image registration device according to the invention may further comprise second registration unit that performs second registration between the target object included in the video and the simulation image based on a result of the first registration, and the display control unit may display the target object included in the video and the simulation image after the second registration on the display unit so as to be superimposed on each other.

In this case, the display control unit may display the boundary image on the display unit, instead of the simulation image, in response to an instruction to display the boundary image at the time of the second registration.

A second image registration device according to the invention comprises: image acquisition unit that acquires a video configured to include two or more images with different imaging times that include a target object to be imaged; simulation image acquisition unit that acquires a simulation image relevant to the target object; boundary image acquisition unit that acquires a boundary image showing a boundary of the simulation image; display control unit that displays the video and the simulation image on display unit; first registration unit that performs first registration between the target object included in the video and the simulation image in response to an instruction of the first registration; and second registration unit that performs second registration between the target object included in the video and the simulation image based on a result of the first registration. The display control unit displays the target object included in the video and the simulation image after the second registration on the display unit so as to be superimposed on each other, and displays the boundary image on the display unit, instead of the simulation image, in response to an instruction to display the boundary image.

In the first and second image registration devices according to the invention, the boundary image acquisition unit may generate the boundary image by extracting a boundary of the simulation image.

In the first and second image registration devices according to the invention, the boundary image may be formed of a broken line, or may be a transparent image.

"Boundary image is formed of a broken line" means that a boundary image is formed of a plurality of line segments. In addition, the distance between the line segments and the length of each line segment do not necessarily need to be fixed, and the distance between the line segments and the length of each line segment may be changed as a one-dot chain line or a two-dot chain line.

"Transparent image" means an image, in which a portion overlapping a boundary image in a video can be seen, when being displayed so as to be superimposed on the video. For example, a boundary image can become a transparent image by setting a predetermined transparency for the boundary image.

In the first and second image registration devices according to the invention, in a case where the target object includes at least one structure, the simulation image may be an image showing three-dimensional shapes of the target object and at least the one structure.

In this case, the boundary image may be an image showing three-dimensional shapes of a boundary of the target object and at least the one structure.

A first image registration method according to the invention includes: acquiring a video configured to include two or more images with different imaging times that include a target object to be imaged; acquiring a simulation image relevant to the target object; acquiring a boundary image showing a boundary of the simulation image; displaying the video and the simulation image on display unit; performs first registration between the target object included in the video and the simulation image in response to an instruction of the first registration; and displaying the boundary image on the display unit instead of the simulation image while an instruction of at least the first registration is given.

A second image registration method according to the invention includes: acquiring a video configured to include two or more images with different imaging times that include a target object to be imaged; acquiring a simulation image relevant to the target object; acquiring a boundary image showing a boundary of the simulation image; displaying the video and the simulation image on display unit; performing first registration between the target object included in the video and the simulation image in response to an instruction of the first registration; performing second registration between the target object included in the video and the simulation image based on a result of the first registration; and displaying the target object included in the video and the simulation image after the second registration on the display unit so as to be superimposed on each other and displaying the boundary image on the display unit, instead of the simulation image, in response to an instruction to display the boundary image.

In addition, non-transitory computer readable medium storing a program causing a computer to execute the first and second image registration methods according to the invention may be provided.

According to the invention, while an instruction of at least the first registration is given, a boundary image is displayed instead of a simulation image. Therefore, by performing the first registration with a target object using the boundary image, it is possible to easily perform the registration between the target object and the boundary image without being obstructed by the simulation image.

By displaying the boundary image instead of the simulation image in response to an instruction to display the boundary image at the time of the second registration, it is possible to easily check whether or not the target object and the boundary image are registrated without being obstructed by the simulation image. In addition, by displaying the boundary image, it is possible to check the state of the target object without being obstructed by the simulation image.

DESCRIPTION OF THE PREFERRED EMBODIMENTS

Figure 1:
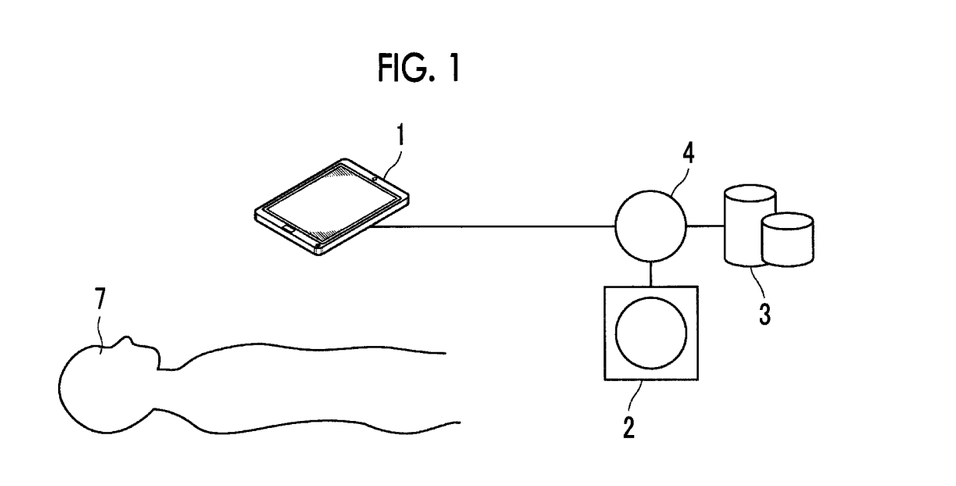
FIG. 1 is a diagram showing the schematic hardware configuration of a surgery assistance system to which an image registration device according to an embodiment of the invention is applied.

Hereinafter, embodiments of the invention will be described with reference to the diagrams. FIG. 1 is a diagram showing the schematic hardware configuration of a surgery assistance system to which an image registration device according to a first embodiment of the invention is applied. As shown in FIG. 1, in this system, an image registration device 1 according to the present embodiment, a three-dimensional imaging apparatus 2, and an image storage server 3 are communicably connected to each other through a network 4.

The three-dimensional imaging apparatus 2 is an apparatus that generates a three-dimensional image V0 showing a part, which is a surgery target in a subject 7, by imaging the part. Specifically, the three-dimensional imaging apparatus 2 is a CT apparatus, an MRI apparatus, a PET apparatus, or the like. The three-dimensional image V0 generated by the three-dimensional imaging apparatus 2 is transmitted and stored in the image storage server 3. In the present embodiment, it is assumed that the surgery target part of the subject 7 is liver, the three-dimensional imaging apparatus 2 is a CT apparatus, and the three-dimensional image V0 of the abdomen of the subject 7 is generated. In addition, the liver that is a surgery target part is a target object.

The image storage server 3 is a computer that stores and manages various kinds of data, and includes a large-capacity external storage device and software for database management. The image storage server 3 performs communication with other devices through the wired or wireless network 4 to transmit and receive image data or the like. Specifically, the image storage server 3 acquires image data, such as the three-dimensional image V0 generated by the three-dimensional imaging apparatus 2, through the network, and stores the image data in a recording medium, such as a large-capacity external storage device, and manages the image data. The storage format of image data or the communication between devices through the network 4 is based on protocols, such as a digital imaging and communication in medicine (DICOM).

The image registration device 1 is realized by installing an image registration program of the invention in one computer. In the present embodiment, a computer is a tablet terminal that is directly operated by a doctor, who is an operator of the apparatus, and that is wirelessly connected to the network 4. The registration program is distributed in a state in which the registration program is recorded in a recording medium, such as a digital versatile disc (DVD) or a compact disk read only memory (CD-ROM), and is installed into the tablet terminal from the recording medium. Alternatively, the registration program is stored in a storage device of a server computer connected to the network or in a network storage device so as to be accessible from the outside, and is downloaded and installed into a tablet terminal when necessary.

Figure 2:
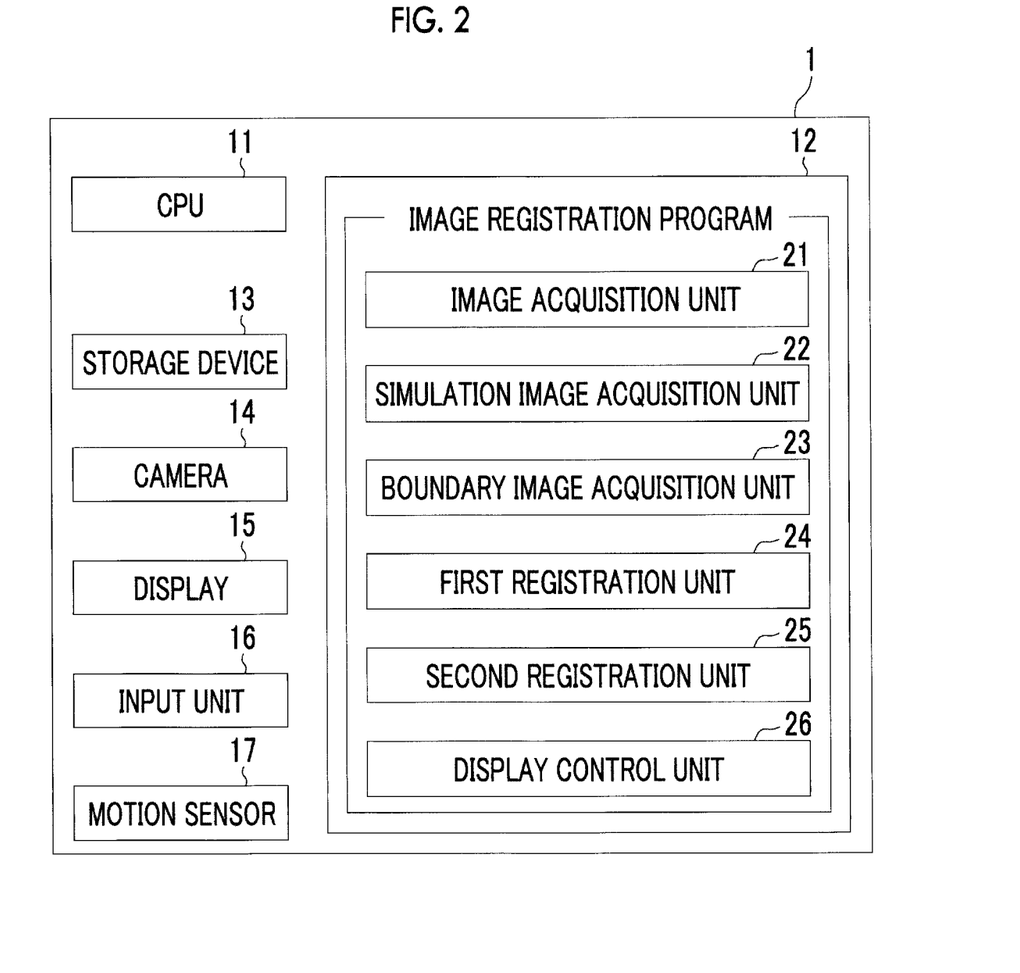
FIG. 2 is a diagram showing the schematic configuration of an image registration device realized by installing an registration program in a tablet terminal.

FIG. 2 is a diagram showing the schematic configuration of an image registration device realized by installing an image registration program in a tablet terminal. As shown in FIG. 2, as the configuration of a standard tablet terminal, the image registration device 1 includes a central processing unit (CPU) 11, a memory 12, a storage device 13, a camera 14, a display 15 such as a liquid crystal display, a touch panel type input unit 16, and a motion sensor 17.

Various kinds of information including the three-dimensional image V0, which has been acquired from the image storage server 3 through the network 4, and the image generated by the processing in the image registration device 1 are stored in the storage device 13.

The camera 14 includes a lens, an imaging device such as a charge coupled device (CCD), an image processing unit that performs processing for improving the image quality on the acquired image, and the like. The doctor acquires an intraoperative video L0 including the liver, which is configured to include two or more images captured at different imaging times, by imaging the liver of the subject 7 after laparotomy, which is a surgery target part in the subject 7 during surgery, using the image registration device 1, that is, the camera 14 of the tablet terminal. The intraoperative video L0 is a motion picture in which intraoperative images T0 are continuous at a predetermined frame rate. The camera 14 corresponds to imaging unit.

The motion sensor 17 is a 9-axis motion sensor that detects the acceleration of three axes of an x axis, a y axis, and a z axis relative to the position of the tablet terminal as a reference, angular velocity of three axes, and the inclination of three axes. Accordingly, the motion sensor 17 detects the movement of the tablet terminal, that is, the movement of the camera 14. The acceleration, the angular velocity, and the inclination detected by the motion sensor 17 are output to the CPU 11 as motion information, and are used in required processing.

In addition, an image registration program is stored in the memory 12. As processing executed by the CPU 11, the image registration program defines image acquisition processing for acquiring the intraoperative video L0 and the three-dimensional image V0, simulation image acquisition processing for acquiring a simulation image S0 of the liver that is a target object included in the intraoperative video L0, a boundary image acquisition processing for acquiring a boundary image B0 showing the boundary of a simulation image, initial registration processing, that is, first registration processing for performing first registration, which is initial registration between the liver included in the intraoperative video L0 and the simulation image S0, in response to a first registration instruction, second registration processing for performing second registration between the liver included in the intraoperative video L0 and the simulation image S0 based on the result of the first registration, and display control processing for displaying the intraoperative video L0, the simulation image S0, and the boundary image B0 on the display 15.

The CPU 11 executes these processes according to the program, so that the tablet terminal functions as an image acquisition unit 21, a simulation image acquisition unit 22, a boundary image acquisition unit 23, a first registration unit 24, a second registration unit 25, and a display control unit 26. In addition, the image registration device 1 may include a processor that performs image acquisition processing, simulation image acquisition processing, boundary image acquisition processing, first registration processing, second registration processing, and display control processing.

The image acquisition unit 21 acquires the intraoperative video L0 including a target part of the subject 7 during the surgery captured by the camera 14 and the three-dimensional image V0. In a case where the three-dimensional image V0 is already stored in the storage device 13, the image acquisition unit 21 may acquire the three-dimensional image V0 from the storage device 13. In the present embodiment, the intraoperative video L0 is acquired when a doctor images the liver from above the subject 7 after laparotomy.

The simulation image acquisition unit 22 generates a simulation image of the liver that is a surgery target part. Accordingly, the simulation image acquisition unit 22 first extracts the liver that is a surgery target part and hepatic arteries, hepatic veins, and lesions, which are included in the liver, from the three-dimensional image V0. The simulation image acquisition unit 22 includes an identifier for identifying whether or not each pixel in the three-dimensional image V0 is a pixel showing the liver and hepatic arteries, hepatic veins, and lesions included in the liver (hereinafter, referred to as the liver and the like). The identifier acquires a plurality of sample images including the liver and the like by machine learning using a method, such as Ada boosting algorithm. The simulation image acquisition unit 22 extracts the liver and the like from the three-dimensional image V0 using an identifier.

Then, the simulation image acquisition unit 22 generates an image showing the three-dimensional shape of the liver and the like as the simulation image S0. Specifically, a projected image obtained by projecting the extracted liver and the like onto a predetermined projection plane is generated as the simulation image S0. Here, the projection plane may be any plane facing the liver of the subject 7 from the front, for example. In addition, as a specific projection method, for example, a known volume rendering method is used.

Figure 3:
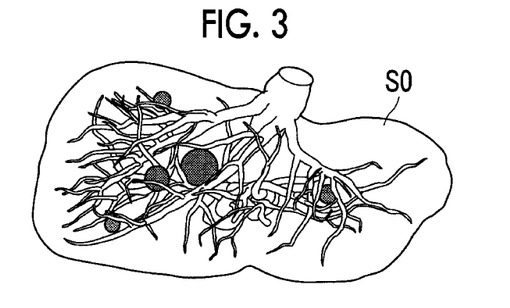
FIG. 3 is a diagram showing a simulation image.

At this time, the simulation image S0 may be generated by defining different colors for the liver and hepatic arteries, hepatic veins, and lesions included in the liver, or the simulation image S0 may be generated by defining different transparencies. For example, red, blue, and green may be set for hepatic arteries, hepatic veins, and lesions, respectively. In addition, the opacity of the liver may be set to 0.1, the opacity of hepatic arteries and hepatic veins may be set to 0.5, and the opacity of lesions may be set to 0.8. In this manner, the simulation image S0 shown in FIG. 3 is generated. Thus, in the simulation image S0, by defining different colors or different opacities for the liver and hepatic arteries, hepatic veins, and lesions included in the liver, it is possible to easily identify the liver and hepatic arteries, hepatic veins, and lesions included in the liver. Alternatively, the simulation image S0 may be generated by defining both different colors and different transparencies. The generated simulation image S0 is stored in the storage device 13.

Figure 4:
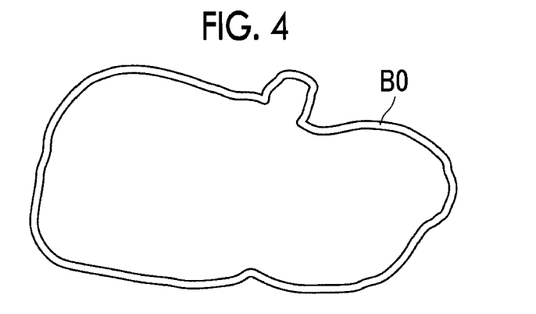
FIG. 4 is a diagram showing an example of a boundary image.

The boundary image acquisition unit 23 acquires the boundary image B0 by extracting the boundary of the simulation image S0 to generate the boundary image B0. In the present embodiment, the simulation image S0 is a projected image showing the three-dimensional shape of the liver. Accordingly, the boundary image acquisition unit 23 generates a two-dimensional image of the liver by drawing the simulation image S0 in a two-dimensional manner using a tuned rendering method, and generates a predetermined range from the boundary as the boundary image B0. FIG. 4 is a diagram showing the boundary image B0. As shown in FIG. 4, the boundary image B0 shows a boundary of the liver included in the simulation image S0. It is preferable that the color of the boundary image B0 is different from the color of the liver included in the intraoperative video L0. For example, it is preferable to set a relatively bright color that is different from the color of internal tissues of the human body, such as white and yellow.

Instead of the tuned rendering method, when generating the simulation image S0 by projecting the three-dimensional image V0, the boundary image acquisition unit 23 may generate, as the boundary image B0, only the region of the surface of the simulation image S0 in which the inner product of a vector toward the projection plane and a normal vector of the surface in the simulation image S0 is a value close to 90°. The region of the simulation image S0 in the three-dimensional image V0 may be covered with a single color, a portion having a large difference from adjacent pixels in the single-color simulation image S0 may be extracted as a boundary, and a region of the predetermined range from the extracted boundary may be generated as the boundary image B0. In addition, a z buffer that is depth information when generating the simulation image S0 by projecting the three-dimensional image V0 onto the projection plane may be used. In this case, a portion whose depth in a direction toward the projection plane is greatly changed may be extracted as a boundary of the simulation image S0 with reference to the z buffer, and the region of a predetermined range from the extracted boundary may be generated as the boundary image B0.

Figure 5:
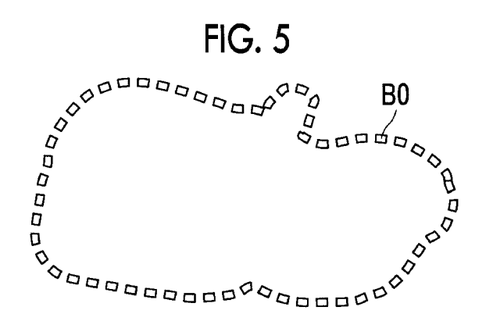
FIG. 5 is a diagram showing an example of a boundary image.
Figure 6:
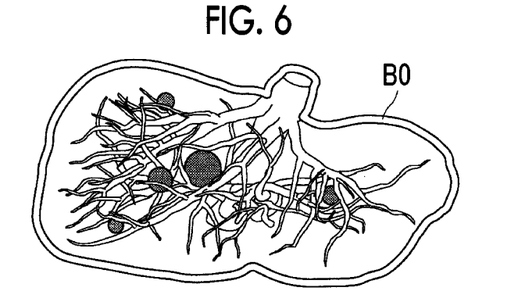
FIG. 6 is a diagram showing an example of a boundary image.

In addition, as shown in FIG. 5, the boundary image acquisition unit 23 may generate the boundary image B0 formed of a broken line. In FIG. 5, the boundary image B0 is generated using a broken line in which a distance between line segments is fixed. However, the distance between the line segments and the length of each line segment may be changed as a one-dot chain line or a two-dot chain line. When displaying the boundary image B0 so as to be superimposed on the intraoperative video L0, the boundary image B0 may be generated so as to be translucent, so that a portion overlapping the boundary image in the intraoperative video L0 can be viewed. In this case, it is preferable to set the transparency to a predetermined value. In addition, as shown in FIG. 6, the boundary image acquisition unit 23 may generate the boundary image B0 that has a boundary of only the liver among the liver included in the simulation image S0 and arteries, veins, and lesions included in the liver and that includes a simulation image of arteries, veins, and lesions other than the liver inside the boundary.

Hereinafter, a process performed in the present embodiment will be described together with the explanation of the first registration unit 24, the second registration unit 25, and the display control unit 26.

Figure 7:
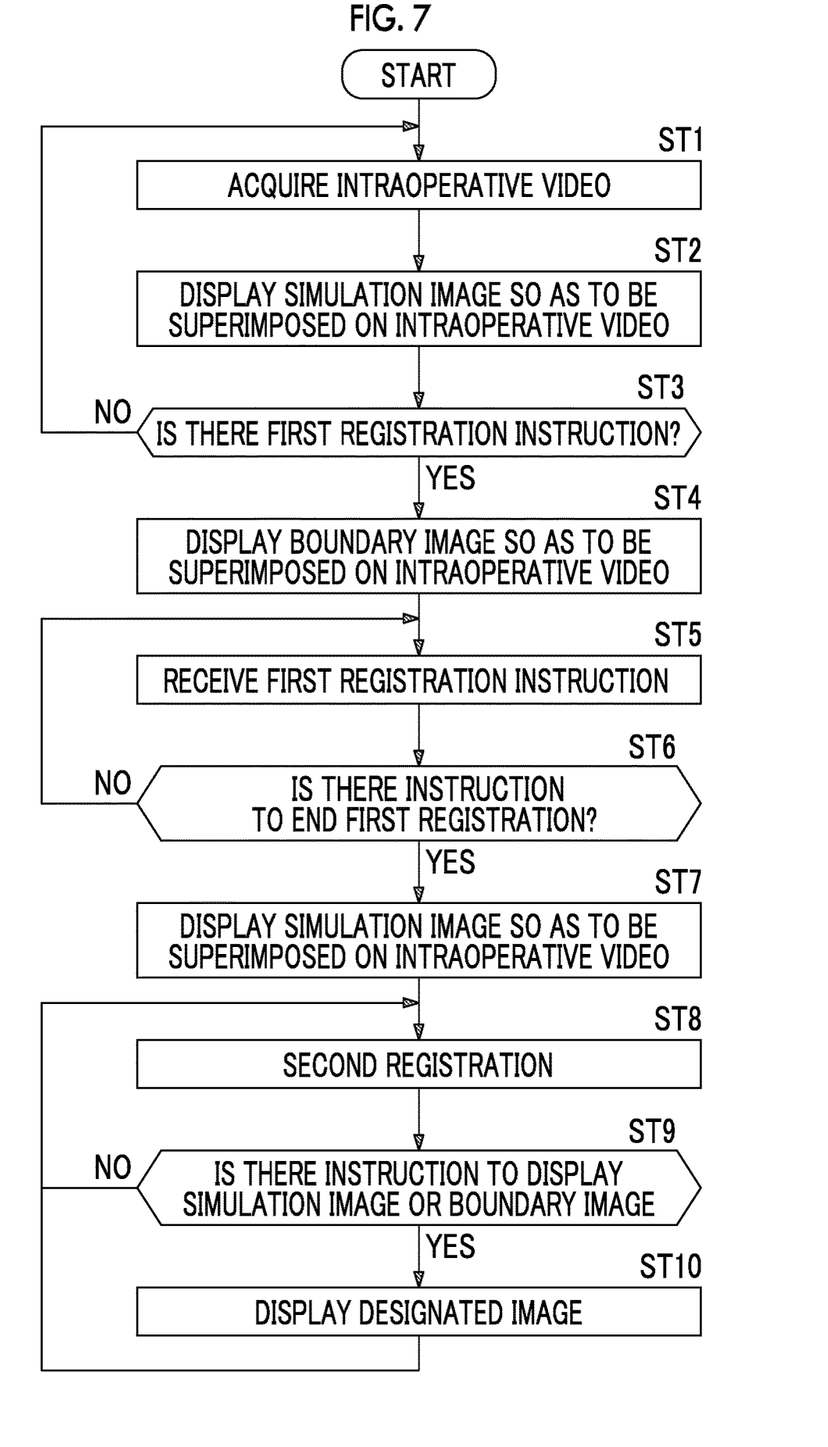
FIG. 7 is a flowchart showing a process performed in the present embodiment.

FIG. 7 is a flowchart showing the process performed in the present embodiment. In addition, it is assumed that the simulation image S0 and the boundary image B0 have already been generated and stored in the storage device 13. First, the intraoperative video L0 is acquired by imaging the liver that is a surgery target part of the subject 7 (step ST1). The intraoperative video L0 is configured to include a plurality of intraoperative images T0 that are sequentially acquired at a predetermined frame rate, such as 30 fps. Then, the display control unit 26 superimposes the simulation image S0 on the intraoperative video L0, and displays the result on a display 15 (step ST2). In this step, the simulation image S0 is displayed at a predetermined position on the display 15.

Then, the first registration unit 24 starts monitoring regarding whether or not there is an instruction of the first registration (step ST3). If the result in step ST3 is positive, the display control unit 26 displays the boundary image B0 instead of the simulation image S0 so as to be superimposed on the intraoperative video L0 (step ST4). Then, the first registration unit 24 receives an instruction of the first registration from a doctor (step ST5). Then, the first registration unit 24 performs the first registration that is an initial registration.

Figure 8:
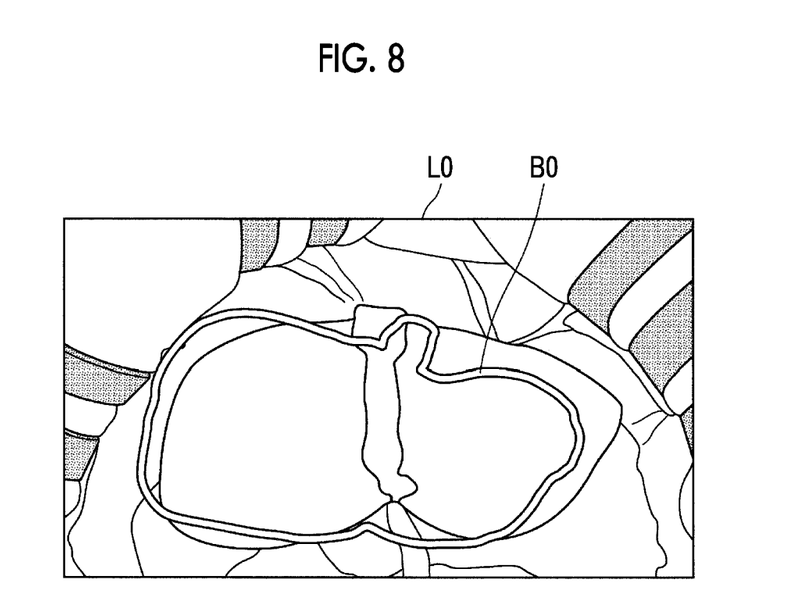
FIG. 8 is a diagram showing an intraoperative image displayed on a display during first registration.

FIG. 8 is a diagram showing an image displayed on the display 15 at the time of the first registration. At the time of the first registration, the display control unit 26 superimposes the boundary image B0 on the intraoperative video L0, and displays the result on the display 15. Parallel movement, rotation, and enlargement and reduction of the displayed boundary image B0 can be realized by operating the input unit 16, that is, by a touch operation on the display 15. In a case where the x and y axes are set on the plane where an image is present and the z axis is set in a direction perpendicular to the image, the simulation image S0 can be rotated in an arbitrary direction of the three axes. In a case where rotation other than the rotation on the xy plane has been made, that is, in a case where rotation around the x axis and/or the y axis has been made, the projection plane of the simulation image S0 is changed. Accordingly, in a case where the projection plane has changed, the simulation image acquisition unit 22 generates the simulation image S0 again, and the boundary image acquisition unit 23 generates the boundary image B0 again. At the time of the first registration, it is preferable to adjust the position of a tablet terminal so that the entire surgical field is included in the intraoperative video L0 as much as possible.

The doctor performs parallel movement, rotation, and enlargement and reduction of the boundary image B0 so that the position of the boundary image B0 matches the position of the liver included in the intraoperative video L0 while watching the intraoperative video L0 and the boundary image B0 displayed on the display 15. Then, when the position of the boundary image B0 matches the position of the liver included in the intraoperative video L0, the first registration is ended by giving an instruction to end the first registration using the input unit 16. An instruction to end the first registration may be given by operating the input unit 16, or by displaying a button for an end instruction on the display 15, or by performing a predetermined operation, such as a double tap. Then, the intraoperative video T0 that is one frame of the intraoperative video L0 displayed on the display 15 at the end of the first registration is stored in the storage device 13 as an initial intraoperative image T1.

In the present embodiment, since a surgery target part is liver, the liver may be excised and moved during the surgery. In the present embodiment, therefore, the initial intraoperative image T1 is displayed on the display 15 at the end of the first registration, and designation of an invariant position that does not move during the surgery is received. For example, in the initial intraoperative image T1 shown in FIG. 9, a part where a surgical instrument, such as forceps 30, is present does not move during the surgery. In the case of excising the left lobe of the liver, the right lobe of the liver does not move during the surgery. In the present embodiment, therefore, designation of an invariant position that does not move during the surgery, such as a position O1 on the edge of the forceps 30 or a position O2 of the right lobe of the liver, is received through the input unit 16, and the invariant position is stored in the storage device 13.

Then, the first registration unit 24 determines whether or not there has been an instruction to end the first registration (step ST6). In addition, the second registration unit 25 may perform the processing of step ST6. If the result in step ST6 is negative, the process returns to step ST5 to continue receiving the designation of the first registration. If the result in step ST6 is positive, the display control unit 26 displays the simulation image S0 instead of the boundary image B0 so as to be superimposed on the intraoperative video L0 (step ST7), and the second registration unit 25 performs second registration based on the result of the first registration that is an initial registration (step ST8).

Figure 10:
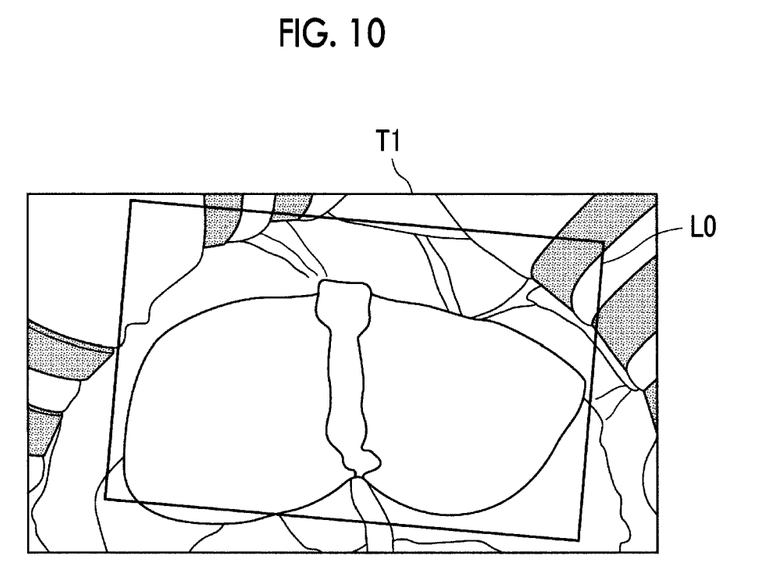
FIG. 10 is a diagram illustrating the shift of the position of an intraoperative video, which is being currently displayed, with respect to an initial intraoperative image.

After the first registration, the doctor advances the surgery. During the surgery, the doctor cannot keep the tablet terminal above the subject 7. For this reason, the imaging of the target part using the tablet terminal is temporarily interrupted. Then, when necessary, for example, in order to check the position of a lesion, the target part is imaged using the tablet terminal. At this time, the position of the tablet terminal is moved from the position where the first registration has been performed, and the imaging of the target object is performed again. In such a situation, the position of the camera 14 is shifted from the position of the initial intraoperative image T1. Therefore, as shown in FIG. 10, the position of the intraoperative video L0 displayed on the display 15 with respect to the initial intraoperative image T1 is shifted. The second registration unit 25 acquires position information indicating a relative position difference between the initial intraoperative image T1 and the newly acquired intraoperative image T0, which is included in the intraoperative video L0, based on the invariant position during the surgery that is included in the intraoperative video L0.

First, in order to acquire the position information, the second registration unit 25 performs template matching between the intraoperative image T0 and the initial intraoperative image T1 with the invariant position as a reference.

Figure 9:
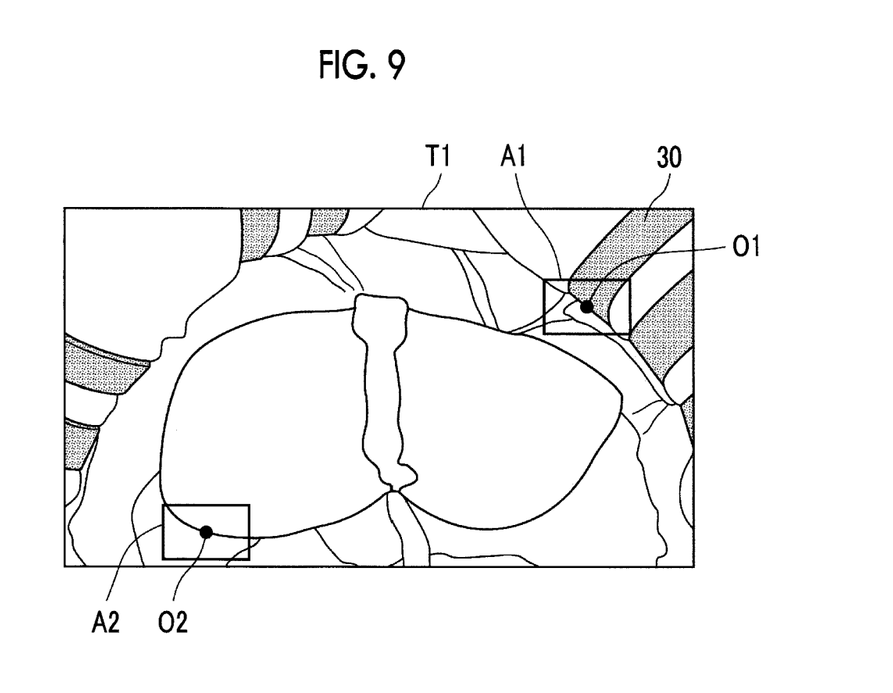
FIG. 9 is a diagram illustrating the setting of a region around an invariant position.

As a method of template matching, it is possible to use a method of setting regions A1 and A2 having invariant positions O1 and O2 at the center, respectively, in the initial intraoperative image T1 as shown in FIG. 9 and calculating at least one of the parallel movement component, the rotational component, and the magnification of the intraoperative image T0 with respect to the initial intraoperative image T1 as position information based on the correspondence relationship between the regions A1 and A2 and the intraoperative image T0. In addition, the rotation means two-dimensional rotation around the z axis (that is, on the xy plane).

Here, the position information indicates a relative position difference between the intraoperative image T0, which is currently displayed, and the initial intraoperative image T1. Accordingly, the position information corresponds to the relative position difference between the current position of the camera 14 and the position of the camera 14 at the time of the first registration.

Figure 11:
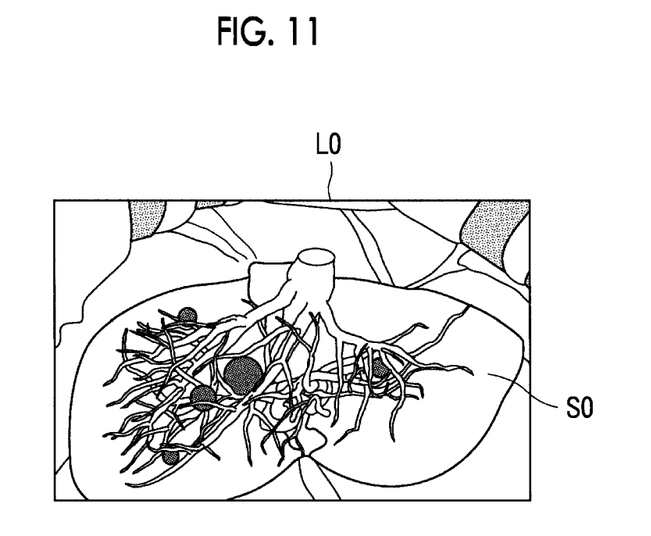
FIG. 11 is a diagram illustrating the superimposed display of a simulation image and an intraoperative video.

The second registration unit 25 aligns the initial intraoperative image T1 and the intraoperative image T0 using the position information, and performs the second registration using the result of the registration. That is, the simulation image S0 is displayed so as to be superimposed on the registrated intraoperative image T0. At this time, parallel movement, rotation, and/or enlargement and reduction of the simulation image S0 are performed based on the position information. As a result, as shown in FIG. 11, the simulation image S0 is displayed so as to be superimposed on the intraoperative video L0 at the same position as the position of registration with the initial intraoperative image T1.

Then, the display control unit 26 determines whether or not there is an instruction to display the simulation image S0 or the boundary image B0 from the doctor (step ST9). If the result in step ST9 is negative, the process returns to step ST8 to continue the second registration. If the result in step ST9 is positive, the display control unit 26 displays the designated image instead of the image, which is currently displayed so as to be superimposed on the intraoperative video L0 (step ST10), and the process proceeds to step ST8. The second registration unit 25 continues the second registration. In a case where the simulation image S0 is displayed so as to be superimposed on the intraoperative video L0, the display control unit 26 displays the boundary image B0. In addition, in a case where the boundary image B0 is displayed so as to be superimposed on the intraoperative video L0, the display control unit 26 displays the simulation image S0.

Thus, in the present embodiment, while an instruction of at least the first registration is given, the boundary image B0 is displayed instead of the simulation image S0. Therefore, by performing the first registration with the liver, which is a target object, using the boundary image B0, it is possible to easily perform the first registration between the target object and the boundary image B0 without being obstructed by the simulation image S0.

In addition, by displaying the boundary image G0 instead of the simulation image S0 in response to an instruction to display the boundary image B0 at the time of the second registration, it is possible to easily check whether or not the liver and the boundary image B0 are registrated without being obstructed by the simulation image S0. In addition, by displaying the boundary image B0, it is possible to check the state of the liver without being obstructed by the simulation image S0.

In the embodiment described above, the boundary image B0 is displayed so as to be superimposed on the intraoperative video L0 in a case where there is an instruction of the first registration. However, the boundary image B0 may be displayed so as to be superimposed on the intraoperative video L0 even before the instruction of the first registration.

In the embodiment described above, the boundary image B0 is displayed so as to be superimposed on the intraoperative video L0 in a case where there is an instruction of the first registration. However, in order to follow the instruction of the first registration, that is, in order to perform parallel movement, rotation, and enlargement and reduction of the boundary image B0, the boundary image B0 may be displayed so as to be superimposed on the intraoperative video L0 while a doctor is performing an operation using the input unit 16, and the simulation image S0, instead of the boundary image B0, may be displayed so as to be superimposed on the intraoperative video L0 while an operation is being interrupted.

In the embodiment described above, the simulation image S0 is displayed so as to be superimposed on the intraoperative video L0 in a case where there is an instruction to end the first registration. However, the boundary image B0 may be continuously displayed so as to be superimposed on the intraoperative video L0.

In the embodiment described above, at the time of the first registration, the boundary image B0 is displayed so as to be superimposed on the intraoperative video L0. However, the first registration may also be performed in a state in which the simulation image S0 is displayed so as to be superimposed on the intraoperative video L0. In this case, in a case where there is an instruction to display the simulation image S0 or the boundary image B0 at the time of the second registration, the boundary image B0, instead of the simulation image S0, may be displayed so as to be superimposed on the intraoperative video L0.

In the embodiment described above, while the second registration is being performed, a position shift may occur between the simulation image S0 and the liver. In such a case, the doctor may give an instruction of the first registration again using the input unit 16. Then, the first registration is performed again by the first registration unit 24.

In the embodiment described above, the intraoperative video L0 and the simulation image S0 or the boundary image B0 are displayed so as to be superimposed on each other in the tablet terminal. However, even at the time of the first registration when displaying the intraoperative video L0 on the head mounted display, the boundary image B0, instead of the simulation image S0, may be displayed so as to be superimposed on the intraoperative video L0. Even in the case of performing the first registration when capturing the intraoperative video L0 using a camera located above the operating table and displaying the image acquired by the capturing on a display in the operating room or a display outside the operating room, the boundary image B0, instead of the simulation image S0, may be displayed so as to be superimposed on the intraoperative video L0. In this case, the image registration device 1 according to the present embodiment is installed in a computer, and initial registration between the intraoperative video L0 and the boundary image B0 is performed by the computer. In the subsequent second registration, the intraoperative video L0 and the simulation image S0 are displayed on a head mounted display connected to the computer or a display of the computer so as to be superimposed on each other.

In the embodiment described above, a projected image of the liver extracted from the three-dimensional image V0 is used as the simulation image S0. However, the simulation image S0 is not limited thereto as long as the information of the outer shape of the liver is included, and a functional three-dimensional image obtained by PET examination, nuclear medical examination, or the like may be used as a simulation image. In addition, a line indicating the resection position, symbols such as arrows, text information such as a name of a part or tissue near the resection position, and the like may be added to the simulation image S0.

In the embodiment described above, the simulation image acquisition unit 22 generates the simulation image S0. However, the simulation image S0 may also be generated by a simulation image acquisition device provided separately from the image registration device 1. In this case, since the simulation image acquisition unit 22 does not need to generate the simulation image S0, it is possible to simplify the configuration of the device.

In the embodiment described above, the boundary image acquisition unit 23 generates the boundary image B0. However, the boundary image B0 may also be generated by a boundary image acquisition device provided separately from the image registration device 1. In this case, since the boundary image acquisition unit 23 does not need to generate the boundary image B0, it is possible to simplify the configuration of the device.

In the embodiment described above, the first registration is performed by performing the parallel movement, rotational movement, enlargement and reduction, and direction change of the boundary image B0 generated from the simulation image S0. However, a plurality of pieces of boundary images B0 generated from a plurality of simulation images in various directions may be prepared, and the boundary image B0 in a direction that matches most the direction of the target part included in the intraoperative video L0 at the time of the first registration may be selected to perform the first registration.

In the embodiment described above, hepatic arteries or the like included in the liver are extracted to be included in the simulation image S0. However, only the liver that is a surgery target part may be extracted, and an image showing the three-dimensional shape of only the liver may be used as the simulation image S0.

In the embodiment described above, the liver is used as a surgery target part. However, surgery target parts are not limited to the liver, and the invention can be applied when performing the first registration between the intraoperative video L0 and the boundary image B0 in a case where an arbitrary part is set as a surgery target.

In the embodiment described above, a surgery target part in the human body is used as a target object. However, when performing registration between a target object, which is included in a video in which a subject is not a human body, and the simulation image S0 of the target object, the boundary image B0 of the target object generated from the simulation image S0 may be used instead of the simulation image S0.

Hereinafter, the effect of the embodiment of the invention will be described.

Since it becomes easy to see the boundary between the target object and the boundary image by generating the boundary image formed of a broken line or the boundary image formed of a transparent image, it is possible to perform the first registration more easily.

What is claimed is:

1. An image registration device, comprising:
a processor configured to
acquire a video configured to include two or more images with different imaging times that include a target object to be imaged by a camera;
acquire a simulation image relevant to the target object by extracting the target object from a three-dimensional image;
generate a boundary of the simulation image by extracting the boundary of the simulation image and acquire a two dimensional boundary image showing the boundary of the simulation images, wherein the boundary image includes a closed curve or a dashed line which represents an outer circumference of the simulation images;
display the video and the simulation image on display unit; and
perform first registration between the target object included in the video and the simulation image in response to an instruction of the first registration input by a user,
wherein in case where an instruction of at least the first registration is given, the processor displays the boundary image, which is matched manually to the target object, on the display unit instead of the simulation image,
wherein in case where the first registration is ended, the processor displays the video and the simulation image on display based on the result of the first registration and receives a designation of an invariant position that does not move during a surgery inputted by the user, and
wherein in case where a position of the camera is shifted from the position where the first registration is performed, the processor performs second registration between the target object included in the video and the simulation image based on the invariant position and a result of the first registration.

2. The image registration device according to claim 1, the processor further configured to:
display the target object included in the video and the simulation image after the second registration on the display unit so as to be superimposed on each other.

3. The image registration device according to claim 2,
wherein the processor displays the boundary image on the display unit, instead of the simulation image, in response to an instruction to display the boundary image at the time of the second registration.

4. The image registration device according to claim 2,
wherein the boundary image is a transparent image.

5. The image registration device according to claim 1,
wherein the boundary image is formed of a broken line.

6. The image registration device according to claim 1,
wherein the boundary image is a transparent image.

7. The image registration device according to claim 1,
wherein, in a case where the target object includes at least one structure, the simulation image is an image showing three-dimensional shapes of the target object and at least the one structure.

8. The image registration device according to claim 7,
wherein the boundary image is an image showing three-dimensional shapes of a boundary of the target object and at least the one structure.

9. An image registration method using the image registration device according to claim 1, comprising:
acquiring a video configured to include two or more images with different imaging times that include a target object to be imaged by a camera;
acquiring a simulation image relevant to the target object by extracting the target object from a three-dimensional image;
generating a boundary of the simulation image by extracting the boundary of the simulation image and acquiring a boundary image showing the boundary of the simulation image, wherein the boundary image includes a closed curve or a dashed line which represents an outer circumference of the simulation image;

displaying the video and the simulation image on display unit;

performing first registration between the target object included in the video and the simulation image in response to an instruction of the first registration input by a user;

displaying the boundary image, which is matched manually to the target object, on the display unit instead of the simulation image, in case where an instruction of at least the first registration is given; while an instruction of at least the first registration-is-given;

displaying the video and the simulation image on display based on the result of the first registration and receives a designation of an invariant position that does not move during a surgery inputted by the user, in case where the first registration is ended; and performing second registration between the target object included in the video and the simulation image based on the invariant position and a result of the first registration in case where a position of the camera is shifted from the position where the first registration is performed.

10. Non-transitory computer readable medium storing an image registration program causing the image registration device according to claim 1 as a computer to execute:

a procedure of acquiring a video configured to include two or more images with different imaging times that include a target object to be imaged by a camera;

a procedure of acquiring a simulation image relevant to the target object by extracting the target object from a three-dimensional image;

a procedure of generating a boundary of the simulation image by extracting the boundary of the simulation image and acquiring a two dimensional boundary image showing the boundary of the simulation image, wherein the boundary image includes a closed curve or a dashed line which represents an outer circumference of the simulation image, a procedure of displaying the video and the simulation image on display unit;

a procedure of performing first registration between the target object included in the video and the simulation image in response to an instruction of the first registration input by a user;

a procedure of displaying the boundary image, which is matched manually to the target object, on the display unit instead of the simulation image, in case where an instruction of at least the first registration is given; while an instruction of at least the first-registration is given;

a procedure of displaying the video and the simulation image on display based on the result of the first registration and receives a designation of an invariant position that does not move during a surgery inputted by the user, in case where the first registration is ended; and a procedure of performing second registration between the target object included in the video and the simulation image based on the invariant position and a result of the first registration in case where a position of the camera is shifted from the position where the first registration is performed.

* * * * *